US008604231B2

(12) United States Patent
Doppelt et al.

(10) Patent No.: US 8,604,231 B2
(45) Date of Patent: Dec. 10, 2013

(54) METAL COMPLEXES FOR CHEMICAL VAPOUR DEPOSITION OF PLATINUM

(75) Inventors: Pascal Doppelt, Noisy-le-Sec (FR); Cyril Thurier, Orleans (FR)

(73) Assignee: Centre National de la Recherche Scientifique, Paris (FR)

( * ) Notice: Subject to any disclaimer, the term of this patent is extended or adjusted under 35 U.S.C. 154(b) by 190 days.

(21) Appl. No.: 13/144,391

(22) PCT Filed: Jan. 8, 2010

(86) PCT No.: PCT/FR2010/000013
§ 371 (c)(1),
(2), (4) Date: Aug. 2, 2011

(87) PCT Pub. No.: WO2010/081959
PCT Pub. Date: Jul. 22, 2010

(65) Prior Publication Data
US 2011/0294672 A1    Dec. 1, 2011

(30) Foreign Application Priority Data

Jan. 15, 2009  (FR) .................................... 09 00165

(51) Int. Cl.
  *C07F 15/00* (2006.01)
  *H01L 39/24* (2006.01)
  *B01J 23/42* (2006.01)
  *C23C 16/00* (2006.01)
(52) U.S. Cl.
  USPC ............ 556/11; 556/136; 505/447; 427/252; 502/339

(58) Field of Classification Search
  USPC ...................... 556/11, 136; 505/447; 502/339; 427/252
  See application file for complete search history.

(56) References Cited

U.S. PATENT DOCUMENTS

| 3,105,084 | A | 9/1963 | Wilkinson |
| 5,104,684 | A | 4/1992 | Tao et al. |
| 6,204,178 | B1 | 3/2001 | Marsh |
| 2002/0000591 | A1 | 1/2002 | Dederian |
| 2002/0090450 | A1 | 7/2002 | Hartner et al. |
| 2003/0049932 | A1 | 3/2003 | Li et al. |
| 2006/0014367 | A1 | 1/2006 | Marsh |

FOREIGN PATENT DOCUMENTS

| GB | 906018 | 9/1962 |
| JP | 8-020870 | 1/1996 |
| JP | 2009-038097 | 2/2009 |
| WO | WO 2007/088292 A1 | 8/2007 |

OTHER PUBLICATIONS

Miller et al., Journal of American Chemical Society, vol. 110, No. 10, pp. 3156-3163 (1988).*

(Continued)

*Primary Examiner* — Porfirio Nazario Gonzalez
(74) *Attorney, Agent, or Firm* — Alston & Bird LLP (57) ABSTRACT

The invention relates to platinum complexes, to a method for preparing the same and to the use thereof for the chemical vapor deposition of metal platinum. The chemical vapor deposition of platinum onto a substrate is made from a platinum organo-metal compound the includes a ligand with a cyclic structure including at least two non-adjacent C=C double bonds, and the platinum organo-metal compound has a square-lane structure in which the platinum is bonded to each of the C=C double bonds of the ligand, thereby forming a (C=C)—Pt—(C=C) of 60° to 70°.

18 Claims, 4 Drawing Sheets

(56) References Cited

OTHER PUBLICATIONS

International Search Report and Written Opinion for International Application No. PCT/FR2010/000013, mailed Sep. 15, 2010.

Appleton, T.G., et al.; "Displacement of norbornadiene (NBD) from PtMe2(NBD) by N-donors, dimethylsulfoxide, and cyanide, and reactions of cis-PtMe2L2 iodomethane"; Journal of Organometallic Chemistry; Elsevier-Sequoia, S.A.; Lausanne, CH; LNKD DOI:10. 1016/0022-328X(86)80119-X,; vol. 303; No. 1; Apr. 1, 1986; pp. 139-149; XP008106261; ISSN: 0022-328X; [retrieved on Apr. 16, 2001]; Abstract.

Appleton, T.G., et al.; "Synthesis of dimethylplatinum(Iv) compounds, [{PtMe2X2}n], [IPtMe2XYln], and, in solution, fac-[PtMe2X(H20)3]<+>, where X and Y are anionic ligands"; Database accession No. EIX97123506713; Canadian Journal of Chemistry; National Research Council of Canada; vol. 74; No. 11; Nov. 1996; pp. 2008-2017; XP008106103; Abstract & Database Compendex [Online]; Engineering Information, Inc., New York, NY, US; Nov. 1, 1996.

Clark, H.C., et al.; "Reactions of (pi-l,5-cyclooctadiene)organoplatinum(II) compounds and the synthesis of perfluoroalkylplatinum complexes"; Journal of Organometallic Chemistry; Jan. 1, 1973; pp. 411-428; XP002598039; p. 421-423; p. 424.

Debaerdemaeker, T., et al.; "Platin -kolhenstoff -a -bidungen mit gehinderte rotation: chloro(2 -alkoxynaphth -l -yl)"; Journal of Organometallic Chemistry; 1988; pp. 91-99; XP008106218; The Nederlands; pp. 93-94; table 2.

Dell'amico, D.B., et al.; "Competition between carbon monoxide and alkenes in chloro complexes of platinum(II)"; Organometallics; Jan. 1, 2005; pp. 4427-4431; XP002598038; p. 4430

Oberbeckmann, N.; "Die Einfflhrung confunktionalisierten Cyclopentadienyl-Liganden an Platin(II)-Zentren fiber Diolefin-Platin-Komplexe"; 2001; XP008106208; pp. 23, 32-33.

Ogawa, A., et al.; "product class 3: organometallic complexes of platinum"; Science of Syntheses; Jan. 1, 2002; pp. 389-437; XP002598040; pp. 402-403

Martin, T.P., et al., Journal of Chemical Vapor Deposition; vol. 11, Issue 3; Mar. 2005; pp. 170-174.

Chen, T.Y., et al.; "2-Methyl-1-hexen-3-yne Lewis Base Stabilized 8-Diketonate Copper(I) Complexes: X-ray Structures, Theoretical Study, and Low-Temperature Chemical Vapor Deposition of Copper Metal"; Journal of Chemistry of Materials; vol. 13; Issue 11: Nov. 2001; pp. 3993-4004.

Story, P.R., et al.; "Synthesis of 7-Methyl- and 7-Phenylnorbornadiene"; The Journal of Organic Chemistry; vol. 28; Issue 6; Jun. 1963; pp. 1716-1717.

Truce, W.E., et al.; "Stereoisomeric 1,2-Bis-(arylmercapto)-ethenes and Corresponding Sulfones"; Journal of the American Chemical Society; vol. 76; Issue 22; Nov. 1954; pp. 5745-5747.

Thurier, C., et al.; "Platinum OMCVD processes and precursor chemistry"; Coordination Chemistry Reviews; vol. 252; Issues 1-2; Jan. 2008; pp. 155-169.

* cited by examiner

METAL COMPLEXES FOR CHEMICAL VAPOUR DEPOSITION OF PLATINUM

FIELD OF THE INVENTION

The invention relates to novel platinum complexes, to a process for preparing them and to their use for the chemical vapor deposition of platinum metal. The invention also relates to a process for manufacturing a platinum film or dispersion, and also to a component of an electronic device and a catalyst comprising such a platinum film or dispersion.

BACKGROUND OF THE INVENTION

Thin platinum films and dispersions of platinum particles are widely used in microelectronics, for example for manufacturing ohmic or Schottky diode contacts, diffusion-barrier films, as coatings for materials subjected to high temperatures and for the manufacture of supported solid catalysts. Among all the metal deposition methods, the method of chemical vapor deposition of an organometallic compound (also known as the MOCVD method or more simply CVD for "metallo-organic chemical vapor deposition") gives very good results in terms of costs, treatment temperatures, durations, covering power and general quality of the deposit.

The possibility of forming a satisfactory metallic deposit via the MOCVD method depends on the volatility of the precursor compound. Specifically, this method requires the possibility of obtaining a high vapor pressure of the precursor compound and high stability of this same compound.

The principle of MOCVD is that of vaporizing a volatile precursor of the metal, namely an organometallic complex, which decomposes thermally on the substrate to form a metallic layer. In practice, the vaporization takes place under pressure and temperature conditions that make it possible to obtain a sufficient precursor vapor pressure for the deposit, while at the same time remaining within its stability range. As regards the substrate, it is heated beyond this stability range, which allows decomposition of the organometallic assembly and the formation of metal particles. The CVD deposition method has various advantages over the other known methods: the thermolysis temperature in CVD of organometallic compounds is 1 to 2 thousand degrees lower than for the other vapor deposition techniques. The films obtained are dense and continuous, which makes it possible to avoid porosity incompatible with good electrical properties. In contrast with the liquid impregnation method, this method is rapid, and impregnation, washing, drying, calcination and activation steps are avoided. Poisoning of the surface and modifications of the activated material during drying are also avoided. It is thus a rapid and economical method for obtaining controlled depositions of good quality.

Various organometallic Pt compounds, which are complexes containing platinum and organic ligands, are currently widely used. Mention may be made especially of: Pt(acac)$_2$, Pt(PF$_3$)$_4$, (cod)PtMe$_2$, MeCpPtMe$_3$ or EtCpPtMe$_3$. These compounds, also referred to herein as precursors, are widely described in the literature.

These known precursors have the following formulae:

Thus, in the present patent application, the following abbreviations denote the following groups:
(acac)$_2$: bis-acetylacetonate,
(cod): 1,5-cyclooctadiene,
(Cp): cyclopentadienyl.

However, each of these precursors has limits that constitute a drawback for their use in an MOCVD process in an industrial context.

Thus, various studies have shown that decomposition problems are encountered during the use of Pt(acac)$_2$: the ligand may decompose without decoordinating the metal, which generally leads to a deposit containing a large amount of impurities.

Pt(PF$_3$)$_4$ leads to a deposit containing fluorine, which is prohibitive for certain applications (Martin T. P. et al., J. Chem. Vap. Deposition, 2005, 11, 170-174).

(cod)PtMe$_2$ is an advantageous precursor, but it has moderate volatility, which makes it necessary to work at higher temperatures compared with the other platinum complexes. Furthermore, with this precursor used in solution, deposits that have unreproducible properties are observed, which suggests a lack of stability of the solution of this precursor during long-term storage.

CpPtMe$_3$ is sensitive to air and moisture.

As regards MeCpPtMe$_3$, it is sensitive to air and moisture, and is expensive.

Its analog EtCpPtMe$_3$ shows better stability, but, just like MeCpPtMe$_3$, it is expensive.

SUMMARY OF THE INVENTION

The invention is directed toward overcoming the drawbacks of the organometallic platinum precursor compounds of the prior art by proposing organometallic platinum precursors that are stable at room temperature but readily decomposable at a moderate temperature, volatile, and of advantageous cost price since they can be manufactured via a process comprising only one or two steps.

To this end, the invention proposes organometallic platinum compounds that comprise a ligand of cyclic structure comprising at least two nonadjacent C=C double bonds, and which have a flat square structure in which the platinum is bonded to each of the C=C double bonds of the ligand forming an angle (C=C)—Pt—(C=C) of between 60 and 70°.

Preferably, the angle (C=C)—Pt—(C=C) is between 64 and 66° and is advantageously equal to about 65°.

In one preferred embodiment of the invention, the ligand of the organometallic compounds of the invention has the formula (I) below:

Formula (I)

in which:
  n represents an integer chosen from 1 and 2,
  when n=1, $R_{1i}$, $R_{1j}$ each represent only one group, when n=2, $R_{1i}$ and $R_{1j}$ each represent two identical or different groups,
  $R_{1a}$, $R_{1b}$, $R_{1c}$, $R_{1d}$, $R_{1i}$ and $R_{1j}$, which may be identical or different, are chosen from: H, a halogen atom, a $C_1$ to $C_4$ alkyl group, a $C_1$ to $C_4$ trialkylsilane group, a $C_2$ to $C_4$ alkenyl group, a $C_1$ to $C_4$ alkyl group bearing one or more OH functions.

The term "halogen atom" means an atom chosen from: F, Cl, I, Br.

The alkyl and alkenyl groups may be linear or branched.

The term "$C_1$-$C_4$ trialkylsilane group" means a silane group formed from an Si atom bearing three identical or different $C_1$-$C_4$ alkyl substituents. Preferably, the three alkyl substituents are identical.

Preferably, in the compounds of formula (I), one or more of the following conditions is satisfied:
  n=1,
  $R_{1b}$, $R_{1c}$, $R_{1d}$ and $R_{1j}$ are all identical and represent H,
  $R_{1a}$ is chosen from: H, Cl, methyl, ethyl, n-propyl, isopropyl, tert-butyl, trimethylsilane, 3-propenyl, ethanol,
  $R_{1i}$ is chosen from: H, methyl, ethyl.

Most preferably, in formula (I), $R_{1a}$ is chosen from: H, methyl, ethyl, n-propyl, isopropyl, trimethylsilane.

According to a preferred embodiment of the invention, the organometallic platinum compounds correspond to formula (II) below:

Formula (II)

in which n and $R_{1a}$, $R_{1b}$, $R_{1c}$, $R_{1d}$, $R_{1i}$ and $R_{1j}$ are as defined above for formula (I), with the same preferred variants, and $R_2$ and $R_3$ are each chosen, independently of each other, from linear $C_1$ to $C_4$ alkyls.

With the exclusion of the case where: n=1, $R_{1a}=R_{1b}=R_{1c}=R_{1d}=R_{1i}=H$, $R_2=R_3=CH_3$, these molecules are novel and constitute a subject of the invention.

Preferably, in formula (II), $R_2$ and $R_3$ are identical and are chosen from: methyl, ethyl.

Organometallic platinum compounds that are particularly preferred for performing the process of the invention are the compounds of formulae (II-A), (II-B), (II-C), (II-D), (II-E) and (II-F) below:

(II-A)

(II-B)

(II-C)

(II-D)

(II-E)

(II-F)

The invention is based on the discovery that the compounds of formula (II) are, surprisingly, more stable at room temperature than organometallic compounds of the same type in which the angle (C═C)—Pt—(C═C) is or is close to 90°.

The organometallic platinum compounds of the invention have a flat square structure around the platinum due to an Ian-Teller effect that is well known for an ion of a transition metal of electron structure $5d^8$ such as $Pt^{2+}$.

Furthermore, the organometallic compounds (II) of the invention are more readily evaporable or sublimable at lower temperatures than those of the prior art, and release the platinum at this moderate temperature while at the same time rapidly volatilizing the carbon elements of the organometallic compounds according to the invention, as is illustrated in the experimental section.

Preferably, the angle (C═C)—Pt—(C═C) is close to 65°, i.e. it is equal to about 65°.

The structure of the compound of formula (II-A) according to the invention, like that of the compound (cod)PtMe₂ of the prior art, is a flat square structure. Scheme 1 below shows the data obtained by X-ray diffraction on monocrystals of these two platinum precursors in which the platinum is in $Pt^{2+}$ form; interatom distances and interbond angles.

Scheme 1: main information obtained by X-ray crystallography on the structure of (II-A) and the compound (cod)PtMe$_2$.

From these data, it was possible to deduce the flat square structure of these two molecules. However, an important difference is that, in the case of the compound of the prior art, the Me-Pt-Me and (C=C)—Pt—(C=C) angles are close to 90° (an angle of 90° corresponds to the ideal flat square configuration) and that in the case of the compound of formula (II-A) of the invention, the rigidity constraints of the norbornadiene ligand and the small distance between the two double bonds impose a smaller (C=C)—Pt—(C=C) angle, of 65.8°.

This constraint, which is greater in the molecule, would have led to a less stable structure and to a smaller bond energy between the platinum and the norbornadiene ligand than for the bond with the cyclo-octadiene ligand of the prior art compound.

However, surprisingly, it was found experimentally that the compound of formula (II-A) is more stable at room temperature while at the same time having better volatility than the compound (cod)PtMe$_2$ of the prior art.

Specifically, $^1$H NMR (nuclear magnetic resonance) studies have shown that a solution of the compound of formula (II-A) degrades less quickly than the (cod)PtMe$_2$ of the prior art. These NMR studies were carried out using $5\times10^{-2}$ M precursor solutions in deuterated chloroform (not dried or degassed) using tetramethylsilane (TMS) as internal standard.

However, these studies also showed that the organometallic compounds of formula (II) of the invention in which the substituent $R_{1a}$ is not H as in the compound of formula (II-A) but a methyl or ethyl or SiMe$_3$ group did not show any pronounced sensitivity toward oxygen and water.

It has thus been found that when the organometallic platinum complexes have a flat square structure in which the (C=C)—Pt—(C=C) angle is between 60 and 70°, their stability at room temperature is increased and their volatility at moderate temperature is increased.

The organometallic platinum compounds of the invention thus have higher stability on storage than the compound (cod)PtMe$_2$ of the prior art.

Specifically, after storage for six days at room temperature under nitrogen, only 5% of the compound of formula (II-A) was decomposed. However, no decomposition was detectable when the compound of formula (II-A) was stored protected from light during this period.

Under the same conditions, 50% of the precursor compound (cod)PtMe$_2$ of the prior art was decomposed.

The influence of the introduction of a substituent onto the norbornadiene ligand on the properties of the compounds of the invention was estimated by observing the aspect of the organometallic compound and by proton NMR spectroscopy.

Thus, when the ligands bonded to platinum (R$_2$ and R$_3$) are a methyl, the compound of formula (II-A) is more stable than the compound of formula (II-B), which is itself more stable than the compound of formula (II-C).

As regards the substituted 7-norbornadienes in which a hydrogen on the carbon in position 7 (the bridge C) is substituted with an Me or Et group, for instance compounds (II-E) and (II-F), it was found that the presence of these groups increases the steric volume of the molecule without having any bearing on the steric interactions of the two CH$_3$ groups bonded to the platinum, which limit the stability of the precursor. Consequently, the volatility of the precursor is increased, its melting point is reduced (in general, liquid precursors are preferred), while at the same time conserving good stability.

The nature of the substituents bonded to platinum, i.e. of R$_2$ and R$_3$, also influences the stability of the organometallic compounds according to the invention.

Thus, when R$_2$ and R$_3$ both represent an ethyl, the compound obtained is less stable than the compound in which R$_2$ and R$_3$ both represent a methyl, for the same substituted or unsubstituted norbornadiene ligand.

However, all the compounds according to the invention are significantly more stable than the compound (cod)PtMe$_2$ of the prior art.

Moreover, the organometallic platinum complexes of the invention are highly volatile at moderate temperatures.

Two distinct processes for manufacturing the compounds of formula (II) were developed. They each constitute a subject of the invention. However, the compounds of formula (II) may also be prepared by applying known processes of the prior art, especially such as those described in Appleton T. G. et al., Journal of Organometallic Chemistry, 303, 1986, 139-149.

A first process for manufacturing an organometallic compound according to the invention (II) is shown in Scheme 2 below.

Scheme 2

(II)

This process comprises a first step of reaction of a ligand of formula (I) as defined above, with $K_2PtCl_4$, in the presence of a halide salt AX in a protic medium. X is chosen from Cl, Br and I. A may be chosen, for example, from K, Na, Ag and $NH_4$, preferably X=I. The medium may simply be water or an alcohol such as methanol, ethanol, propanol or butanol, an acid such as aqueous acetic acid solution, or a mixture of these solvents. In a second step, the compound thus obtained reacts with an organometallic compound of formula $R_2M$ and/or an organometallic compound of formula $R_3M'$ in which $R_2$ and $R_3$ are as defined above and M, M' are metal atoms.

Preferably, in this process, the halide salt AX is KI.

Preferably also, in the formula $R_2M$ and/or the formula $R_3M'$, the metal M and/or M' is chosen from Li, Na, Mg, Al and Sn, and the protic medium is a mixture of water and sec-propanol.

Most preferably, in formula $R_2M$ or formula $R_3M'$, the metal M and/or M' is lithium, Li.

Preferably, $K_2PtCl_4$ and the norbornadiene derivative are introduced in substantially equivalent molar amounts. Advantageously, the first reaction step of this process takes place in the presence of an excess of salt AX relative to the reagents $K_2PtCl_4$ and to norbornadiene, advantageously between 3 and 5 molar equivalents of salt AX relative to the reagents $K_2PtCl_4$ and to norbornadiene.

Another process for manufacturing an organometallic compound of the invention (II) is described in Scheme 3 below:

Scheme 3

This one-step process consists in reacting, at room temperature, a ligand of formula (I) as defined above with $K_2PtCl_4$ and an organometallic compound of formula $R_2M$ and/or an organometallic compound of formula $R_3M'$, in which $R_2$ and $R_3$ are as defined for the compounds of formula (II) above, and M, M' are chosen from metals, in a polar aprotic solvent.

Preferably, in this other process, the polar aprotic solvent may be chosen from ethers such as tetrahydrofuran (THF), dioxane and halogenated solvents such as chloroform or dichloromethane. In formula $R_2M$ and/or formula $R_3M'$, the metal M or M' is advantageously lithium, Li. A catalyst AX of the halide salt type (having the same definition as above) such as KI may advantageously be used, but its presence is not imperative.

These two processes have, relative to the known processes of the prior art that may be applied to the novel molecules of the invention, the advantage of being very simple and of having good yields, and thus of being readily industrializable.

Another subject of the invention is the process for depositing a platinum film or platinum particles onto a support, this process comprising at least one step of chemical vapor deposition of platinum starting with at least one precursor as defined above and especially starting with a compound of formula (II) on a support.

The chemical vapor deposition comprises at least two steps: a first step of vaporization of the precursor, under conditions that do not affect its stability, and a second step of decomposition of the precursor to platinum on a support.

It is possible to carry out vaporization of the pure precursor compound, whether it is liquid or solid at room temperature, or of the precursor compound dissolved in a solvent.

Among the solvents that may be used to perform the process of the invention, the preferred solvents are organic compounds that are liquid at room temperature and up to about 200° C. under normal pressure conditions, which do not react either with the precursor or with the support, and which are resistant to oxidation. By way of example, mention may be made of cyclic hydrocarbon solvents, for instance cyclohexane or tetrahydrofuran, and aromatic solvents such as mesitylene, xylene or toluene, or alternatively n-octane.

When the precursor is used in the form of a solution in an organic liquid, the precursor concentration of the solution is advantageously greater than or equal to $10^{-3}$ mol/l. When a very dilute solution of precursor is used, the formation of a discontinuous deposit of platinum particles is favored, whereas higher concentrations promote the formation of a continuous film. The dilution of the precursor solution also influenced the size of the crystallites formed. During implementation of the process for depositing platinum layers onto a support, the composition containing the precursor such as (II) is sent into a vaporization device via which it is introduced into a deposition chamber at high temperature which contains the support onto which the platinum layer is to be deposited. For example, a gas is bubbled into the reservoir containing the precursor compound such as (II) and this gas entrains the precursor compound into the vapor phase.

Usually, before its arrival in the vaporization device, the composition is maintained in a reservoir at room temperature. Vaporization of the precursor compound such as (II) may be performed using various devices known to those skilled in the art. For example, mention may be made of the device described in T. Y. Chen et al., Chem. Mat. 2001, 13, 3993, sold by the company Jipelec under the name "Infect System for injecting and evaporating liquid precursors in pure or solution form".

When the precursor compound is liquid or when it is in solution, the process of liquid injection of organometallics by CVD (DLI-MOCVD) as described in WO 2007/088 292, may be used for its introduction into the deposition chamber. The principle of DLI-MOCVD is derived from standard CVD systems. The reactive species are brought into liquid form and are injected at high pressure via injectors. This process allows the morphology of the particles to be controlled as a function of the production parameters (the mass of product injected, the injection frequency, the solvent for the precursor and the deposition time) and enables easy implementation at the industrial scale.

The precursor compound is thus, via any of the methods mentioned above, introduced into the deposition chamber. The support or substrate onto which the deposition is to take place is present in this chamber. The precursor compound is then subjected to a decomposition, which brings about its deposition on the support.

The substrate onto which the layer of platinum is deposited may be a supraconductive material with a high Tc (critical temperature), a ceramic, especially a dense ceramic or a porous ceramic, a heat-resistant polymer, a glass, MgO, a perovskite such as $LaAlO_3$, Ni, Si, AsGa, InP, SiC and SiGe. The platinum layer may be deposited onto said support as a first layer or as an $x^{th}$ layer of metallization for electronic devices requiring several levels of metallization, x being an integer greater than or equal to 2. The support may be constituted by one of the abovementioned materials per se, or alternatively by one of these materials bearing one or more intermediate layers. By way of example of intermediate layers, mention may be made of metal films (for example a film of Ni), an organic layer (for example a layer of a polymer material), diffusion layers constituted by at least one material chosen, for example, from TiN, TiSiN, Ta, TaN, TaSiN, WN and WSiN. In the case of deposition of a dispersion, a support serving for mechanical strength and comprising at least one electrically conductive microporous layer, also known as a diffusion layer, is chosen. For example, the support is advantageously chosen from textiles comprising a carbon-bearing microporous surface layer: the porous carbon of the diffusion layer onto which is performed the deposition is made, for example, of carbon, graphite or is formed from nanotubes. The carbon may be of Vulcan XC 72 type or of Shawanagan type.

Various conditions, including activation of the substrate, promote deposition onto the substrate relative to deposition onto the walls of the chamber.

In particular, according to the ALD (atomic layer deposition) process a reactive gas that promotes the decomposition of the precursor is injected into the deposition chamber.

According to the invention, the chamber may be placed:

under a neutral atmosphere using a gas chosen, for example, from: $N_2$, Ar, He, or under an atmosphere of oxygen optionally mixed with a neutral gas such as nitrogen (US 2002/0 000 591; U.S. Pat. No. 6,750,110), oxygen having the advantage of promoting the combustion of the organic materials, or under a hydrogen atmosphere (U.S. Pat. No. 5,130,172), which promotes decomposition and influences the size and shape of the crystallites, or under an ozone atmosphere, and under a pressure preferentially of between $10^{-3}$ and 1000 mbar.

Any of the CVD processes known to those skilled in the art for activating the substrate may be used, and especially: heat activation, laser-induced chemical vapor deposition (LCVD) (JP8020870), UV-induced chemical vapor deposition (U.S. Pat. No. 6,204,178; US 2006/0 014 367), plasma-induced chemical vapor deposition (PECVD), ion beam-assisted chemical vapor deposition (IACVD) (U.S. Pat. No. 5,104,684), electron beam-induced chemical vapor deposition (EB-CVD), or fluidized-bed chemical vapor deposition (FBCVD).

These methods are described in their principle and with practical embodiments in C. Thurier and P. Doppelt, Coord. Chem. Rev. 252, (2008) 155-169.

In all cases, the temperature of the substrate to be coated is higher than or equal to the decomposition temperature of the precursor. The temperature in the deposition chamber is higher than or equal to the vaporization temperature of the precursor and less than or equal to the decomposition temperature of the precursor. When the deposition is performed in the presence of plasma, it suffices for the support intended to receive the platinum layer to be maintained at the same temperature as the evaporator. In the absence of plasma, it is preferable for the support to be at a temperature higher than that of the chamber, the temperature difference being at least equal to 20° C. and preferably at least equal to 50° C., so as to avoid the deposition of platinum on the walls of the reactor.

The vaporization and decomposition temperatures of the precursor may be readily determined for each compound, as will be shown in the experimental section.

A sequential deposition comprising at least one step that promotes nucleation and at least one step that promotes growth of the film may be envisaged (US 2002/0 000 591).

Several activation methods may be combined so as better to control the quality of the deposit.

The thickness of the platinum layer that is deposited on the support depends on the concentration of the precursor composition, such as (II), the flow rate of this composition during passage into the vaporization device, the vaporization time, and the respective temperatures in the reactor and on the support. In general, less concentrated compositions and/or lower flow rates are used to obtain isolated particles and thin layers, and more concentrated compositions and/or higher flow rates are used to obtain thick layers. The term "thin layer" generally means a layer with a thickness of less than or equal to 50 nm, known as the nucleation layer. The term "thick layer" generally means a layer with a thickness of between 50 nm and 10 μm.

To obtain thick layers, it is possible to use the pure product or compositions in a solvent with a high dissolution coefficient, at a precursor concentration close to saturation. The concentration must remain less than the saturation value, so as to avoid reprecipitation of the precursor, which would have the effect of hampering the vaporization.

To obtain thin layers or for dispersions of platinum, it is possible to use the pure product or solvents in which the solubility of the precursor is lower. An organic liquid that is not a solvent for the precursor and that is chemically inert with respect to the precursor may also be used to dilute a precursor composition according to the invention.

It may also be envisioned for the process of the invention to include the use of a sensor for evaluating the amount of reagent gas ($O_2$, $H_2O$, $N_2O$, $O_3$, etc.) to be supplied in order to decompose the organic residues of the precursor) that are adsorbed onto the surface when the deposition rate becomes too low (US 2003/0 049 932).

The use of the process of the invention for the deposition of platinum layers by CVD makes it possible to obtain good-quality deposits that show good adhesion to the substrate onto which they are deposited.

This process makes it possible especially to make a selective deposition of platinum onto certain areas of the support, while avoiding depositing it on other portions of this same support (US 2002/0 090 450).

In conclusion, the organometallic compounds of the invention allow the manufacture of platinum films or dispersions of platinum particles that show good stability toward oxygen and moisture and also good stability on storage at room temperature, preferably in the dark. Their decomposition temperature is low enough to allow the deposition of platinum films at 250° C. by virtue of a pronounced catalytic effect of the formed platinum. The films obtained are of very high purity.

Thus, the films obtained by means of the compounds of the invention have excellent catalytic properties.

A subject of the invention is also a process for producing an electronic component, comprising at least one step of chemical vapor deposition of platinum from at least one precursor, especially (II), as described above.

A subject of the invention is also a process for producing a supported platinum-based solid catalyst, comprising at least one step of chemical vapor deposition of platinum from at least one precursor, especially (II), as described above.

The process of the invention more particularly concerns the production of fuel cells. In this case, a deposition of platinum in the form of isolated particles is preferred.

It also concerns the production of electrodes that may be used in microelectronics, in devices such as sensors, advanced microprocessors, ferroelectric memories, light-emitting devices, junctions, DRAM (dynamic random access memory), FeRAM (ferroelectric random-access memory). In this case, a deposition of platinum in the form of a continuous film is preferred.

BRIEF DESCRIPTION OF THE DRAWINGS

Experimental Section

DETAILED DESCRIPTION OF THE INVENTION

Example 1

One-Step Synthesis of the Compound of Formula (II-B): (Etnbd)PtMe₂

Scheme 4

830 mg of K₂PtCl₄, 20 mL of THF distilled over sodium and benzophenone, and 600 µL (510 mg) of ethyl-norbornadiene are placed in a dry Schlenk tube under argon. At room temperature, 7 mL of 1.6 M MeLi are added. Vigorous stirring is maintained for 24 hours at room temperature.

At 0° C., 30 ml of diethyl ether are added, followed by a solution of 500 mg of NH₄Cl in 20 ml of distilled water. The mixture is extracted and the organic phase is washed with twice 20 mL of water. The ether phase is dried with MgSO₄ and a spatula-full of active charcoal is added. The resulting mixture is filtered and the solvents are evaporated off.

Mass obtained: 574 mg (brown to colorless liquid).

Yield: 83%.

Physicochemical Characterization:

(Etnbd)PtMe₂:

¹H NMR (400.132 MHz, CDCl₃):

δ(ppm): 5.12 (tt, 1H, 20 Hz, 4 Hz); 4.95 (tt, 1H, 19 Hz, 4 Hz); 4.69 (td, 1H, 20 Hz, 3 Hz); 3.94 (s, 1H); 3.81 (s, 1H); 2.22 (m, 2H); 1.59 (q, 2H, 6 Hz); 1.13 (t, 3H, 6 Hz); 0.73 (t, 3H, 44 Hz); 0.65 (t, 3H, 44 Hz)

¹³C NMR (100.622 MHz, CDCl₃):

δ(ppm): 111.8; 88.4; 84.8; 73.1; 52.3; 50.0; 25.1; 12.6; 3.45.

Example 2

Synthesis of the Ethylnorbornadiene Ligand of the Compound of Formula (II-B)

Scheme 5

100 mL of THF distilled over sodium and benzophenone are placed in a 250 mL dry three-necked flask under argon, followed by addition of 7.2 g of tBuOK and 8 mL of norbornadiene. The addition of the norbornadiene leads to the dissolution of the tBuOK. The mixture is cooled to −80° C., and 20 mL of 1.6 M n-BuLi are added dropwise over 30 minutes. The resulting mixture is allowed to warm to −40° C. and maintained at this temperature for 30 minutes. The mixture is returned to −80° C., and aqueous NH$_4$Cl solution at 0° C. is added dropwise. The resulting mixture is allowed to warm slowly to room temperature and is stirred overnight.

100 mL of water are added and the mixture is extracted with twice 100 mL of diethyl ether. The organic phase is washed with twice 100 mL of water. The resulting phase is dried with MgSO$_4$ and filtered, and the solvents are evaporated off. The product is distilled under slightly reduced pressure.

Mass obtained: 2.4 g (colorless liquid)

Yield: 62%

Physicochemical Characterization:

Etnbd:

$^1$H NMR (400.132 MHz, CDCl$_3$):

δ(ppm): 6.76 (s, 2H); 6.10 (s, 1H); 3.49 (s, 1H); 3.27 (s, 1H); 2.20 (m, 2H); 1.96 (dd, 2H, 14 Hz, 6 Hz); 1.00 (t, 3H, 7.5 Hz).

$^{13}$C NMR (100.622 MHz, CDCl$_3$):

δ(ppm): 160.7; 144.0; 142.4; 132.2; 73.4; 68.0; 53.5; 50.0; 24.7; 11.8.

Example 3

Two-Step Synthesis of the Compound of Formula (II-A): (nbd)PtMe$_2$

Step 1: Synthesis of (nbd)PtI$_2$

Scheme 6

20 g of K$_2$PtCl$_4$ are weighed out in a round-bottomed flask, 220 mL of water are added and the mixture is stirred until dissolution is complete. 33 g of KI are added and the mixture is stirred for 15 minutes at room temperature. 225 mg of SnCl$_2$.2H$_2$O, 120 mL of isopropanol and 15 mL of norbornadiene are then added. The resulting mixture is stirred at room temperature for 40 hours. The medium is concentrated by evaporating off the isopropanol on a rotary evaporator under vacuum. The residue is filtered on a sinter funnel, and washed with water and then with cold methanol. The product is dried under vacuum for several hours.

Mass: 26.6 g; yield: 99%.

Step 2: Synthesis of (nbd)PtMe$_2$

Scheme 7

10 g of (nbd)PtI$_2$ are placed in a 250 mL three-necked flask, followed by addition of 140 mL of distilled Et$_2$O. At −80° C. (acetone-cardice bath), 25 mL of 1.6 M MeLi are added dropwise. The bath is allowed to warm slowly to −20° C. (over about 3 hours), and the acetone bath is then removed for 1 hour.

Ice-cold aqueous NH$_4$Cl solution (20 g in 200 mL of water) is prepared in a large beaker, and the reaction medium is poured therein. The phases are allowed to separate by settling, and the organic phase is washed with twice 150 mL of water. The resulting phase is dried over MgSO$_4$, a spatula-full of animal black is added, the resulting mixture is stirred and filtered, and the solvents are evaporated off. A very pale yellow solid is obtained.

The product may also be purified by chromatography on a column of alumina, eluting with an ether/pentane mixture (1:1). A sublimation step also leads to excellent purity.

Mass: 5.757 g; yield: 98%.

Physicochemical Characterization:

(nbd)PtMe$_2$:

$^1$H NMR (400.132 MHz, CDCl$_3$):
δ(ppm): 5.00 (t, 4H, 20 Hz); 3.96 (s, 2H); 1.55 (s, 2H); 1.50 (s, 2H); 0.67 (t, 6H, 44 Hz)
$^{13}$C NMR (100.622 MHz, CDCl$_3$):
δ(ppm): 87.3 (t, 23 Hz); 71.8 (t, 22 Hz); 48.1 (t, 20 Hz); 4.0 (t, 406 Hz).

Example 4

Synthesis of the Compounds of Formulae (II-E) and (II-F): (7-Me-nbd)PtMe$_2$ and (7-Et-nbd)PtMe$_2$

Starting Materials for the Synthesis of the Substituted 7-norbornadienes.

The ligands (7-Me-nbd) and (7-Et-nbd) may be synthesized according to a method described previously (P. R. Story, S. R. Fahrenholtz, *Journal of Organic Chemistry*, 1963, 28, 1716-1717).

1,2-Bis(p-tolylsulfonyl)ethene and 1,2-bis(p-tolyl-mercapto)ethene used as starting materials were synthesized according to a method described previously (W. E. Truce, R. J. McManimie, J. Am. Chem. Soc., 1954, 76, 5745-5747).

Preparation of the Novel Substituted 7-norbornadienes:
The substituted 7-norbornadienes were synthesized in two steps: (i) the Diels-Alder reaction of substituted cyclopentadienes with 1,2-bis(p-tolylsulfonyl)ethene and (ii) the reductive elimination of the anionic species TolylSO$_2$— with the Na—Hg amalgam in basic medium.

Scheme 8: Diels-Alder reaction for preparing the substituted 7-norbornadienes giving sulfonated intermediates.

Intermediate Sulfonated Products Prepared from Methylcyclopentadiene (MeCp)

0.5 g of di-p-toluenesulfonylethylene (1.5 mmol) and 20 mL of toluene are placed in a 100 mL three-necked flask. A solution of 3.0 g (37 mmol) of methylcyclopentadiene freshly cracked by distillation from the dimer (MeCp)$_2$ in 10 mL of toluene is added dropwise to this solution heated to reflux. This reaction mixture is stirred at reflux for 10 minutes and at room temperature for 3 hours. The colorless solid product (0.45 g) that precipitates is recovered by filtration.

Yield=72.5% (based on the di-p-toluenesulfonyl-ethylene).

Melting point=248-250° C.
(TLC: CH$_2$Cl$_2$/MeCOOEt solvent=9/1: Rf=0.68)
$^1$H NMR (400.132 MHz, CDCl$_3$): δ (ppm) 7.82 (m, CH of the Ph), 7.31 (m, CH of the Ph), 6.35 (CH=), 3.17 (CH of the Cp), 2.43 (CH$_3$ of the Ph), 2.15 (CH of the Cp), 2.91 (CH—SO$_2$Ts), 1.23 (CH$_3$ of the Cp).

Intermediate Sulfonated Products Prepared from Ethylcyclopentadiene (EtCp)

The reaction conditions are similar to those used when MeCp is the starting material above, except for the stirring time at room temperature, which is 4 hours instead of 3.

The product obtained is a white solid: yield=46.5%. Melting point: 216-220° C.
$^1$H NMR (400.132 MHz, CDCl$_3$): δ (ppm) 7.88 (CH of the Ph), 7.31 (CH of the Ph), 6.02 (CH=), 2.94 (CH of the Cp), 2.49 (CH$_3$ of the Ph), 2.0-1.8 (CH of the Cp), 1.12 (t, J=7.5 Hz, CH$_3$ of the Et), 0.77 (t, 7.5 Hz, CH$_2$ of the Et).

Reaction for Removal of the p-Tolylsulfonyl

Scheme 9: Reaction for synthesis of the substituted 7-norbornadienes 3 mmol of one of the products synthesized previously (products obtained from the Diels-Alder reaction) and 6.0 g of NaH$_2$PO$_4$ in 80 mL of MeOH are placed in a 250 mL round-bottomed flask. This mixture is placed under argon and stirred. Next, after addition of 10 g of Na—Hg amalgam (5% Na), the suspension is stirred for 18 hours at room temperature under Ar. The amalgam is removed by decantation. A colorless solution containing a white precipitate is then obtained, to which are added 100 mL of deionized water. The suspension is then filtered. 40 mL of saturated NaCl solution are then added to the filtrate and the new precipitate formed is removed by filtration. The filtrate is then extracted with three times 50 mL of pentane. The organic phase obtained is washed three times with saturated aqueous NaCl solution (30 mL) and then dried over MgSO$_4$ and filtered. The pentane is then removed on a rotary evaporator, and the expected colorless liquid product is recovered.

Characerization:

7-methylbicyclo[2.2.1]heptane-2,5-diene (Me-nbd)

+Yield=37.5%
+GC-MS: Retention time=1.14 min; m/z=105, 91, 79, 65, 51
+$^1$H NMR (400.132 MHz, CDCl$_3$): δ (ppm) 5.54 (t, J=4 Hz, 4×CH=), 3.10 (s, 2×-CH), 2.15 (m, 1×-CH), 1.21 (s, 1×-CH$_3$)

7-Ethylbicyclo[2.2.1]heptane-2,5-diene (Et-nbd)

+Yield=35%
+$^1$H NMR (400.132 MHz, CDCl$_3$): δ (ppm) 5.13 (4×CH=), 2.94 (2×CH), 2.0 (1×CH bridge), 1.13 (1×CH$_3$ ethyl) and 0.78 (1×CH$_2$ ethyl).

Synthesis of the Platinum Precursors (II-E) and (II-F)

Compounds (II-E) and (II-F) were synthesized according to the protocol described above in example 3.

(7-Me-nbd)PtI₂

Yield=60.2%.
Solid yellow product with a melting point of 128-130° C.
$^1$H NMR (400.132 MHz, CDCl₃): δ (ppm) 5.66 (t, J=4 Hz, 4×CH═), 3.10 (s, 2×-CH), 2.15 (m, 1×-CH), 1.21 (s, 1×-CH₃)

(7-Et-nbd)PtI₂

Yield=70.5%.
Solid yellow product with a melting point of 140-142° C.
$^1$H NMR (400.132 MHz, CDCl₃): δ (ppm) 5.35 (4×CH═), 2.97 (2×CH), 2.08 (1×CH of the bridge), 1.15 (1×CH₃ ethyl) and 0.70 (1×CH₂ ethyl).

(7-Me-nbd-)PtMe₂ (II-E)

Yield=60%
Yellow liquid with a melting point in the region of −15° C.
$^1$H NMR (400.132 MHz, CDCl₃): δ (ppm) 5.08 (t, J=4 Hz, 4×CH═), 3.10 (s, 2×-CH—), 2.05 (m, 1×-CH—), 1.21 (s, 1×-CH₃ of the nbd-Me), and 0.717 (s, 2×-CH₃) ppm (7-Et-nbd)PtMe₂ (II-F)

Yellow liquid with a melting point in the region of −15° C.

Example 5

Physicochemical Characterization of the Compound of Formula (II-C): (TMSnbd)PtMe₂

Compound (II-C) was prepared in accordance with the protocol of Example 1.

(TMSnbd)PtMe₂:

$^1$H NMR (400.132 MHz, CDCl₃):
δ(ppm): 5.11 (td, 1H, 21 Hz, 4 Hz); 4.90 (tt, 1H, 22 Hz, 4 Hz); 4.68 (tt, 1H, 20 Hz, 4 Hz); 3.72 (s, 1H); 3.58 (s, 1H); 1.50 (dd, 2H, 53 Hz, 9 Hz); 0.59 (t, 3H, 46 Hz); 0.53 (t, 3H, 46 Hz); 0.01 (s, 9H)

$^{13}$C NMR (100.622 MHz, CDCl₃):
δ (ppm): 154.6 (s); 144.57 (s); 143.7 (s); 101.3 (t, 20 Hz); 99.4 (t, 24 Hz); 91.3 (t, 25 Hz); 87.4 (25 Hz); 74.8 (t, 25 Hz); 53.8 (t, 25 Hz); 51.6 (t, 25 Hz); 7.3 (td, 409 Hz, 163 Hz); 0 (s).

Example 6

Study by TGA of the Compounds of the Invention for Deducing Information Regarding their Volatility and their Stability Principle:
TGA studies were undertaken on the organometallic compounds of the invention and compared with those of the literature products.

All the experiments were performed under argon with a temperature increase ramp of 10° C. per minute.

The loss of mass observed is attributed jointly to the volatilization of the precursor and to the decomposition (partial or total) of the precursor, followed by rapid evaporation of the organic residues.

It may be estimated that during total decomposition of the precursor, i.e. with removal of all the organic ligands and substituents, these ligands and substituents are instantly volatilized due to their good volatility. The loss of mass observed is thus directly linked to the decomposition kinetics. During partial decomposition, nonvolatile carbon originating from the ligand residues may remain in the platinum bulk. Part of the loss of mass may be linked to evaporation of the precursor without decomposition.

Results:
The curves obtained are shown in FIG. 1.

Figure 1:
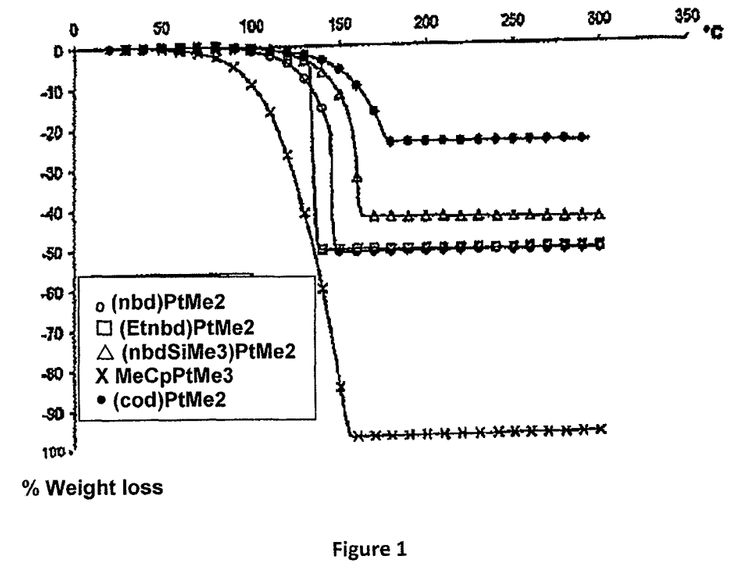
FIG. 1 shows the curves obtained by thermo-gravimetric analysis (TGA) for the precursors of formulae (II-A), (II-B) and (II-C) according to the invention, in comparison with the precursors of the prior art.

As may be seen in FIG. 1, among the organometallic compounds of the invention, the prior art compound MeCpPtMe₃ has the most specific behavior: on increasing the temperature, the mass decreases virtually exponentially to reach 2% of the initial mass at 160° C. This demonstrates the very good volatility of this precursor, but also the fact that its decomposition is negligible up to this temperature.

By comparison, the mass of the organometallic platinum compound of the prior art (cod)PtMe₂ decreases up to 76% of the initial mass. This value remains largely above the initial mass of platinum contained in the precursor, which is 58%. The prior art precursor (cod)PtMe₂ is therefore not very volatile and the residual solid contains at least 24% carbon.

By comparison, the organometallic compounds of the invention decompose at moderate temperatures and without production of carbon-based residues.

Specifically, FIG. 1 shows that the mass of compound of formula (II-A) of the invention decreases up to 52%, below the theoretical mass of platinum, which is 61%.

This demonstrates the good volatility of this precursor, at least 18% of which has evaporated, and indicates a low carbon content.

As regards the compound of the invention of formula (II-B), the results are fairly similar to those obtained with the compound of formula (II-A), with a final mass of 51% as opposed to 56% for the theoretical mass of platinum, i.e. at least 9% of precursor evaporated.

As regards the compound of formula (II-C), its mass at the end of the experiment is 57%. It remains above the initial mass of platinum, which is 50%, which demonstrates the incorporation of carbon and silicon into the residue.

Example 7

Study of the Stability of Compounds (II-A) and (II-B)

Surprisingly, the thermogravimetric analysis revealed that the organometallic compound of formula (II-A) according to the invention was not only the most stable at room temperature, but also at a decomposition temperature (which corresponds to the temperature at which the decomposition is fastest) lower than the compounds of the prior art.

Figure 2:
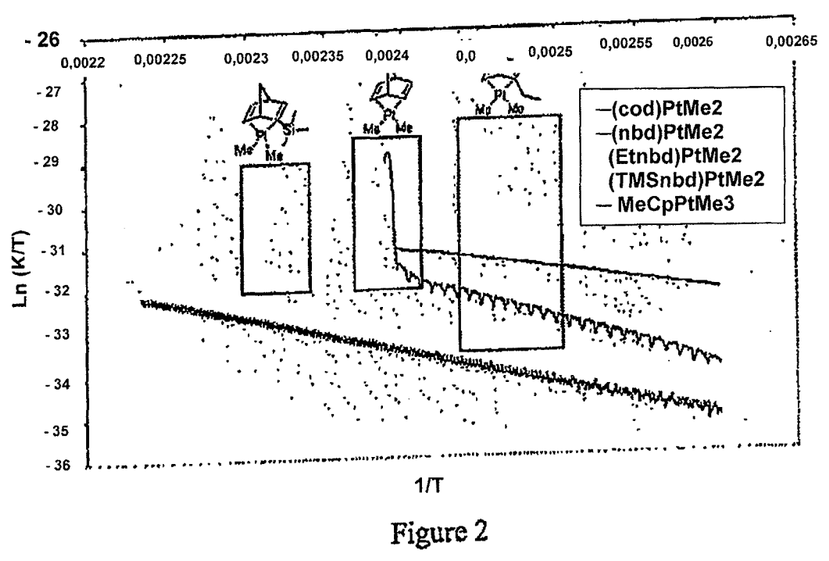
FIG. 2 shows the Eyring graph for the precursors of formulae (II-A), (II-B) and (II-C) according to the invention, in comparison with that of the precursors of the prior art.

However, all the organometallic compounds of the invention have a complex decomposition kinetics profile in which two distinct processes were revealed, which clearly appear when the Eyring-Polanyi curves are plotted. These curves are shown in FIG. 2. As may be seen in FIG. 2, an abrupt loss of mass at about 140° C. is observed, particularly for (nbd)PtMe$_2$ and (Etnbd)PtMe$_2$.

In the case of zero-order kinetics, straight lines must be obtained by plotting Ln(k/T) as a function of 1/T, since the following applies:

$$\operatorname{Ln} \frac{k}{T} = \frac{-\Delta H^{\neq}}{R} \cdot \frac{1}{T} + \operatorname{Ln} \frac{k_5}{h} + \frac{\Delta S^{\neq}}{R}$$

In the case of a loss of mass via the process of evaporation of the precursor, the kinetics for the loss of mass must follow a similar trend, the expression for the pressure of a pure substance being similarly linked to the exponential of the temperature. A commonly used expression of vapor pressure for a pure substance is, for example:

$$\ln(Pv) \approx a + \frac{b}{T} + c \cdot \ln(T)$$

The evaporation component of the precursor in the observed loss of mass should therefore have little effect on the general aspect of the curves.

The Eyring-Polanyi curve obtained with the prior art compound MeCpPtMe$_3$—which evaporates without decomposing—follows a virtually linear trend, which validates the preceding approximation.

Whereas this plot does indeed show a straight line in the case of the prior art precursor (cod)PtMe$_2$, the graphs obtained with the precursors of the invention show two distinct parts: a straight line for the low temperatures, and then a jump corresponding to a sudden increase in the rate above a transition temperature. The existence of these two processes demonstrates a change of mechanism linked to the appearance of a new species. One explanation would be that the solid platinum formed then serves as catalyst for the decomposition of the precursors of the invention. The "bumpy" shape of the curves also suggests a heterogeneous process.

The important fact is that this "catalytic" decomposition is not observed with the other precursors of the prior art, which implies particular properties of the platinum formed with the precursors of the invention: purity, size of the crystals and/or an inhibition effect observed, for example with the cod ligand but not with the ligands (I) of the invention.

Example 8

Chemical Vapor Depositions of Platinum Using the Compounds of Formulae (II-A) and (II-B) According to the Invention The depositions of platinum were performed using a laboratory chemical vapor deposition machine equipped with a vaporization system starting with liquid phase sold by the company Jipelec under the name "Infect system for injecting and evaporating liquid precursors in pure form or in solution form". The samples were heated on an SiO$_2$/Si support (monocrystalline silicon of size 1×1 cm$^2$ covered with 100 nm of SiO$_2$) in the middle of a glass belljar placed in an oven. A vacuum line was connected to an oxygen trap and to a pump. Mounted on the belljar was a preheated evaporation chamber to which two gas inlets and a pressurized liquid injector were connected. Toluene was chosen as solvent for manufacturing 0.1 M solutions of the precursors, which were vaporized at a rate of 0.67 mL·min$^{-1}$. The pressure was maintained at 1 mbar. The two gas inlets delivered, respectively, 40 sccm N$_2$ and 15 sccm O$_2$. The temperatures were set at 80° C. for the evaporation chamber and at 100° C. for the oven. The deposition rate depends on the temperature, such that a temperature of the substrate of 300° C. was preferred to obtain deposits of suitable thickness.

Example 9

Study of the Deposition Rates

The phenomenon observed in Example 6 is confirmed by the deposition rates obtained with the precursors of the invention (nbd)PtMe$_2$ and (Etnbd)PtMe$_2$, which are, under identical conditions, markedly superior to those observed with (cod)PtMe$_2$.

In order to check whether the difference in reactivity between (cod)PtMe$_2$ and (nbd)PtMe$_2$ came from a pronounced inhibition effect due to a strong interaction of the ligand released during the decomposition of the precursor with the formed solid platinum, the deposition rates obtained with solutions of:
  precursor (cod)PtMe$_2$ (prior art),
  precursor (nbd)PtMe$_2$ (compound of formula (II-A) of the invention),
  precursor (nbd)PtMe$_2$+5 equivalents of free cod ligand,
  precursor (nbd)PtMe$_2$+5 equivalents of free nbd ligand,
were compared.

Under identical deposition conditions, i.e. using 20 mL of a 0.1 M solution in toluene, vaporized over 30 minutes with a vaporizer at 80° C., an oven at 100° C., and samples at 300° C. A vector gas that is a mixture of: N$_2$ 40 sccm, O$_2$ 15 sccm, was also used. The total pressure was about 5 mbar, and the rates obtained are:
  precursor (cod)PtMe$_2$: 0.3 nm·min$^{-1}$
  precursor (nbd)PtMe$_2$: 2.0 nm·min$^{-1}$
  precursor (nbd)PtMe$_2$+5 equivalents of free cod ligand: 0.83 nm·min$^{-1}$
  precursor (nbd)PtMe$_2$+5 equivalents of free nbd ligand: 0.83 nm·min$^{-1}$ These results show that the addition of free ligand has an inhibition effect on the growth of the film. They also demonstrate that this influence of the free ligand is identical in the case of free cod and of free nbd. The difference in reactivity therefore cannot be attributed to the interaction of the free ligand with the solid platinum.

The difference in reactivity is thus very probably linked to properties of the platinum crystallites formed, for instance their high purity.

Example 10

Figure 3:
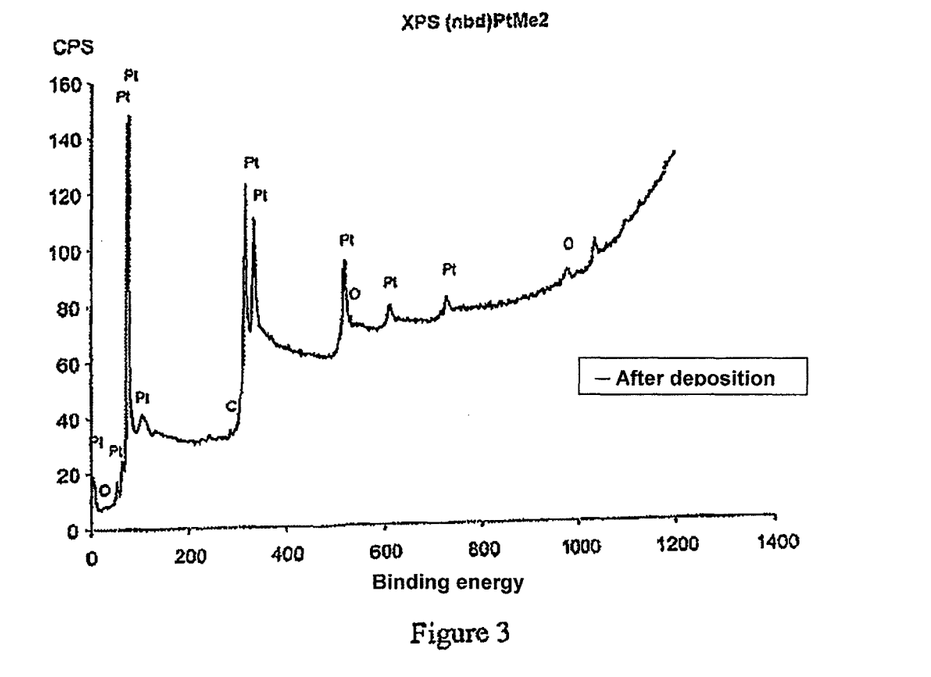
FIG. 3 shows the spectrum obtained by X-ray induced photoelectron spectroscopy (XPS) of a platinum film obtained using the compound of formula (II-A) according to the invention.
Figure 4:
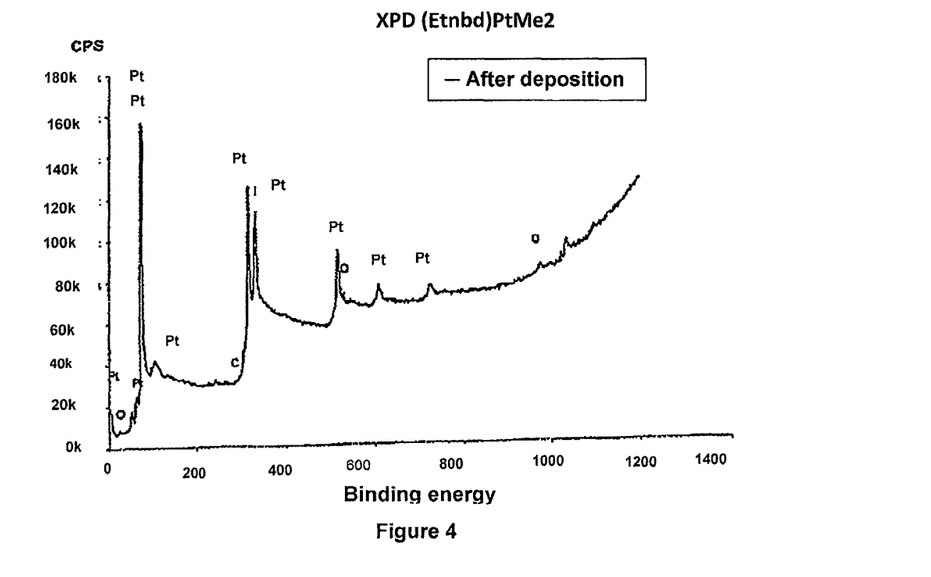
FIG. 4 shows the spectrum obtained by X-ray induced photoelectron spectroscopy (XPS) of a platinum film obtained using the compound of formula (II-B) of the invention.
Figure 5:
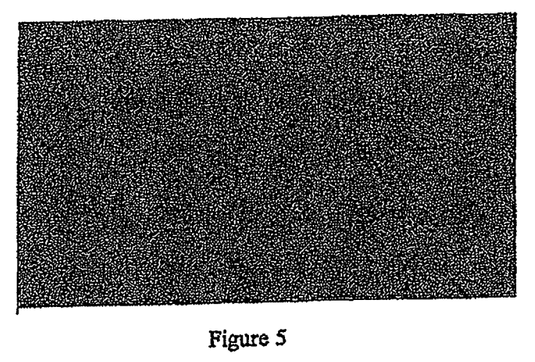
FIG. 5 is a photograph taken by scanning electron microscopy (SEM) of a film obtained using the compound of formula (II-A) according to the invention.
Figure 6:
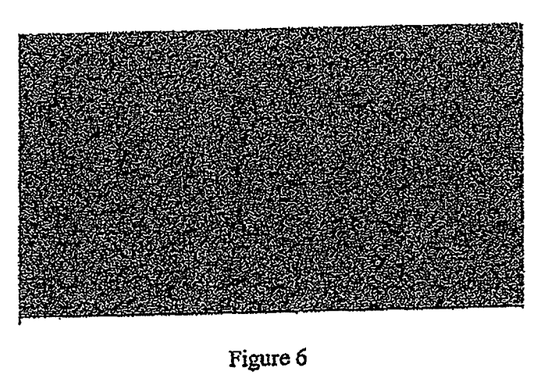
FIG. 6 is a photograph taken by scanning electron microscopy (SEM) of a platinum film obtained using the compound of formula (II-B) of the invention.

Characterization by Scanning Electron Microscopy and X-Ray Induced Photoelectron Spectroscopy Analysis It is seen from FIGS. 3 and 4 that the platinum films obtained are very pure and from FIGS. 5 and 6 that they are very homogeneous.

The good purity of the films obtained was demonstrated via XPS measurements on the films obtained, which demonstrate a very low carbon content.

The spectrum obtained with the compound of formula (II-A) is shown in FIG. 3 and the spectrum obtained with the compound of formula (II-B) is shown in FIG. 4.

An analysis of the surface by grazing incidence X-rays also demonstrated that the films were composed of small crystallites 6-7 nm in diameter.

These results show that the compounds or precursors of the invention have good stability toward oxygen and moisture. Their heat stability depends, itself, on the steric bulk around the metal. The decomposition temperature is low enough to deposit films at 250° C. by virtue of a pronounced catalytic effect of the formed platinum.

Importantly, the films obtained have very good purity with little incorporation of carbon into the formed films. Specifically, the data obtained by X-ray induced photoelectron spectroscopy of the platinum film obtained using the compound of formula (II-A) and for the platinum film obtained using the compound of formula (II-B), which are shown, respectively, in FIGS. 3 and 4, reveal that the films contain oxygen but virtually no carbon.

The platinum films are very pure and contain a small amount of bound oxygen, probably in the form of $PtO_2$. Specifically, the energies observed for the $O_2$ peaks are different at the surface and in the bulk. Carbon is present only at the surface, probably on account of the exposure to air.

The films obtained are also very homogeneous, as may be seen in FIGS. 5 and 6.

FIG. 5, which is a photograph taken by scanning electron microscopy of a platinum film obtained using the compound of formula (II-A) as precursor, shows that the film obtained, which has a thickness of 60 nanometers here, is smooth and continuous.

FIG. 6, which is a scanning electron microscopy photograph of the film obtained using the compound of formula (II-B) as precursor, shows that the film obtained, which in this case has a thickness of 80 nanometers, is also smooth and continuous, although less smooth and less continuous than the film obtained with the compound of formula (II-A).

Example 11

Comparisons Between II-A and II-D

Stability in Air:

Precursor II-E, which is a yellow liquid at room temperature, is more stable in air than II-A since it can be stored for one week in air at room temperature without decomposition.

Figure 7:
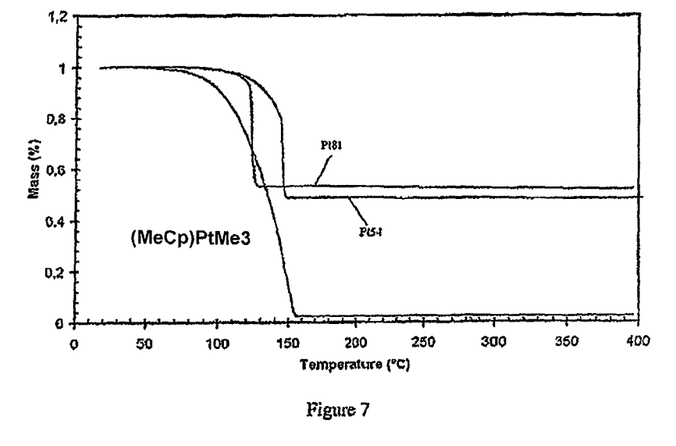
FIG. 7 shows the curves obtained by thermo-gravimetric analysis (TGA) comparative for the platinum precursors II-E (Pt81), II-A (Pt54) and (MeCp)PtMe₃ (Ar flow rate: 10 sccm; 10° C./minute).

Heat Stability:

In the thermogravimetric analysis illustrated by FIG. 7 (argon flow rate of 10 sccm, 10° C./min), a decomposition of the precursor II-E is observed at and above approximately ~120° C. with formation of platinum in the form of a black powder, instead of ~145° C. for II-A and ~155° C. for (MeCp) $PtMe_3$. The lowering of the decomposition temperature of the precursor may prove to be important for certain applications for depositions onto heat-sensitive supports.

Volatility

TABLE 1

Temperatures at which 5%, 10% and 50% by mass of a precursor is evaporated

| Precursors (° C.) | $T_{5\%}$ (° C.) | $T_{10\%}$ (° C.) | $T_{50\%}$ (° C.) |
|---|---|---|---|
| (MeCp) $PtMe_3$ | 91 | 101 | 135 |
| II-A | 122 | 133 | Decomposition |
| II-E | 120 | 122.5 | Decomposition |

Table 1 above gives the temperatures at which 5%, 10% and 50% by mass of the precursor is evaporated for the three different precursors: (MeCp)$PtMe_3$, II-A and II-E. The $T_{5\%}$, and $T_{10\%}$ values for (MeCp)$PtMe_3$ are markedly lower than those for II-A and II-E. This shows that (MeCp)$PtMe_3$ is much less volatile than the two precursors of the norbornadiene family. For the latter, II-E appears to be more volatile than II-A since the $T_{5\%}$ is similar for these two precursors but the $T_{10\%}$ for II-E is lower than that for II-A.

II-E is thus very promising as a precursor for the MOCVD deposition of platinum. This precursor, which is liquid at room temperature, is very stable in air and volatile. Furthermore, it is more heat-"sensitive" than II-A and than the commercial precursor (MeCp)$PtMe_3$. Consequently, it may be hoped to obtain platinum deposits at lower temperatures using this precursor.

The invention claimed is:

1. A process for depositing a platinum film or platinum particles onto a support, this process comprising at least one step of depositing platinum via chemical vapor deposition onto a support using at least one organometallic platinum compound, wherein:
   the organometallic platinum compound comprises a ligand of cyclic structure comprising at least two non-adjacent C═C double bonds, and
   the organometallic platinum compound has a flat square structure in which the platinum is bonded to each of the C═C double bonds of the ligand forming a (C═C)—Pt—(C═C) angle of between 60 and 70°.

2. The process as claimed in claim 1, in which the (C═C)—Pt—(C═C) angle is between 64 and 66°.

3. The process as claimed in claim 1, in which the ligand corresponds to formula (I) below:

Formula (I)

in which:
   n represents an integer chosen from 1 and 2,
   when n=1, $R_{1i}$, $R_{1j}$ each represent only one group, when n=2, $R_{1i}$ and $R_{1j}$ each represent two identical or different groups,
   $R_{1a}$, $R_{1b}$, $R_{1c}$, $R_{1d}$, $R_{1i}$ and $R_{1j}$, which may be identical or different, are chosen from: H, a halogen atom, a $C_1$ to $C_4$ alkyl group, a $C_1$ to $C_4$ trialkylsilane group, a $C_2$ to $C_4$ alkenyl group, a $C_1$ to $C_4$ alkyl group bearing one or more OH functions.

4. The process as claimed in claim 1, in which the organometallic platinum compound corresponds to formula (II) below:

Formula (II)

in which:
   n represents an integer chosen from 1 and 2, when n=1, $R_{1i}$ and $R_{1j}$ each represent only one group, when n=2, $R_{1i}$ and $R_{1j}$ each represent two identical or different groups, $R_{1a}$, $R_{1b}$, $R_{1c}$, $R_{1d}$, $R_{1i}$; and $R_{1j}$, which may be identical or different, are chosen from: H, a halogen atom, a $C_1$ to $C_4$ alkyl group, a $C_1$ to $C_4$ trialkylsilane group, a $C_2$ to $C_4$ alkenyl group, and a $C_1$ to $C_4$ alkyl group bearing one or more OH functions, $R_2$ and $R_3$ are chosen, independently of each other, from linear $C_1$ to $C_4$ alkyls.

5. The process as claimed in claim 3, in which one or more of the following conditions is satisfied:

n=1,

$R_{1b}$, $R_{1c}$, $R_{1d}$ and $R_{1j}$ are all identical and represent H,

$R_{1a}$ is chosen from: H, Cl, methyl, ethyl, n-propyl, isopropyl, tert-butyl, trimethylsilane, 3-propenyl, ethanol,

$R_{1i}$ is chosen from: H, methyl, ethyl.

6. The process as claimed in claim 4, in which $R_2$ and $R_3$ are identical and are chosen from: methyl, ethyl.

7. The process as claimed in claim 1, in which the organometallic platinum compound is chosen from the following list:

(II-A)

(II-B)

(II-C)

(II-D)

(II-E)

(II-F)

8. The process as claimed in claim 1, in which the support is chosen from: a supraconductive material with a high Tc, a ceramic, a heat-resistant polymer, a glass, MgO, a perovskite Ni, Si, AsGa, InP, SiC, SiGe, a textile comprising a carbon-bearing microporous surface layer.

9. The process as claimed in claim 1, in which the support comprises one or more intermediate layers chosen from: metal films, an organic layer, diffusion layers constituted by at least one material chosen from TiN, TiSiN, Ta, TaN, TaSiN, WN, WSiN, carbon, graphite and nanotubes.

10. The process as claimed in claim 1, in which the support is placed in a chamber:
under a neutral atmosphere,
or
under an oxygen atmosphere optionally mixed with a neutral gas,
or
under a hydrogen atmosphere,
or
under an ozone atmosphere.

11. The process as claimed in claim 1, in which the support is subjected to at least one activation chosen from: a heat activation, a laser activation, a UV activation, a plasma activation, an ion-beam activation, an electron-beam activation.

12. A process for producing an electronic component, comprising at least one step of chemical vapor deposition of platinum as claimed in claim 1.

13. A process for producing a solid catalyst based on supported platinum, comprising at least one step of chemical vapor deposition of platinum as claimed in claim 1.

14. A process for producing fuel cells, comprising at least one step of chemical vapor deposition of platinum as claimed in claim 1.

15. An organometallic platinum compound corresponding to formula (II) below:

Formula (II)

in which:
n represents an integer chosen from 1 and 2,
when n=1, $R_{1i}$ and $R_{1j}$ each represent only one group, when n=2, $R_{1i}$ represents two identical or different groups,

$R_{1a}$, $R_{1b}$, $R_{1c}$, $R_{1d}$, $R_{1i}$ and $R_{1j}$, which may be identical or different, are chosen from: H, a halogen atom, a $C_1$ to $C_4$ alkyl group, a $C_1$ to $C_4$ trialkylsilane group, a $C_2$ to $C_4$ alkenyl group, and a $C_1$ to $C_4$ alkyl group bearing one or more OH functions, $R_2$ and $R_3$ are chosen, independently of each other, from linear $C_1$ to $C_4$ alkyls, with the exclusion of the case where:
$n=1$, $R_{1a}=R_{1b}=R_{1c}=R_{1d}=R_{1i}=R_{1j}=H$, $R_2=R_3=CH_3$.

16. The compound as claimed in claim 15, which is chosen from:

(II-B)

(II-C)

(II-D)

(II-E)

(II-F)

17. A process for manufacturing an organometallic platinum compound corresponding to formula (II) below:

Formula (II)

in which:
  n represents an integer chosen from 1 and 2,
  when $n=1$, $R_{1i}$ and $R_{1j}$ each represent only one group, when $n=2$, $R_{1i}$ and $R_{1j}$ each represent two identical or different groups,
  $R_{1a}$, $R_{1b}$, $R_{1c}$, $R_{1d}$, $R_{1i}$ and $R_{1j}$, which may be identical or different, are chosen from: H, a halogen atom, a $C_1$ to $C_4$ alkyl group, a $C_1$ to $C_4$ trialkylsilane group, a $C_2$ to $C_4$ alkenyl group, and a $C_1$ to $C_4$ alkyl group bearing one or more OH functions,
  $R_2$ and $R_3$ are chosen, independently of each other, from linear $C_1$ to $C_4$ alkyls, this process comprising a first step of reacting a ligand of formula (I) with $K_2PtCl_4$ in the presence of a halide salt AX in a protic medium, and a second step in which the compound thus obtained reacts with an organometallic compound of formula $R_2M$ and/or an organometallic compound of formula $R_3M'$ in which M and M' are metal atoms chosen from Li and Na, in accordance with Scheme 2:

Scheme 2

18. A process for manufacturing an organometallic platinum compound corresponding to formula (II) below:

Formula (II)

in which:
  n represents an integer chosen from 1 and 2,
  when $n=1$, $R_{1i}$ and $R_{1j}$ each represent only one group, when $n=2$, $R_{1i}$ and $R_{1j}$ each represent two identical or different groups,
  $R_{1a}$, $R_{1b}$, $R_{1c}$, $R_{1d}$, $R_{1i}$ and $R_{1j}$, which may be identical or different, are chosen from: H, a halogen atom, a $C_1$ to $C_4$ alkyl group, a $C_1$ to $C_4$ trialkylsilane group, a $C_2$ to $C_4$ alkenyl group, and a $C_1$ to $C_4$ alkyl group bearing one or more OH functions,
  $R_2$ and $R_3$ are chosen, independently of each other, from linear $C_1$ to $C_4$ alkyls, this process comprising at least one step in which a ligand of formula (I) is reacted, at room temperature, with $K_2PtCl_4$ and an organometallic compound of formula $R_2M$ and/or an organometallic compound of formula $R_3M'$, in which M and M' are chosen Li and Na, in a polar aprotic solvent, optionally in the presence of a catalyst AX of the halide salt wherein X is chosen from Cl, Br and I and A is chosen from K, Na, Ag and $NH_4$, in accordance with Scheme 3: